United States Patent
Bailey

(10) Patent No.: US 6,627,182 B2
(45) Date of Patent: *Sep. 30, 2003

(54) TOPICAL TREATMENT FOR SKIN AND NAILS

(75) Inventor: Mary L. Bailey, 535 Plumosa Ave., Clearwater, FL (US) 33756

(73) Assignee: Mary L. Bailey, Clearwater, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 3 days.

(21) Appl. No.: 09/962,638

(22) Filed: Sep. 25, 2001

(65) Prior Publication Data

US 2003/0059486 A1 Mar. 27, 2003

(51) Int. Cl.⁷ .............................. A61K 6/00; A61K 7/00; A61K 7/04
(52) U.S. Cl. ......................................... 424/61; 424/401
(58) Field of Search ................................... 424/61, 401

(56) References Cited

U.S. PATENT DOCUMENTS 6,200,570 B1 * 3/2001 Diwan et al. ............ 424/195.1

FOREIGN PATENT DOCUMENTS

EP 0 923 937 * 6/1999

OTHER PUBLICATIONS

J M Watt, The Medicinal and Poisonous Plants of Southern and Eastern Africa, 1962, E. & S. Livingstone Ltd., 2$^{nd}$ Edition.*

* cited by examiner

Primary Examiner—Carlos Azpuru
Assistant Examiner—S. Howard
(74) Attorney, Agent, or Firm—Dennis G. LaPointe; Mason Law, P.A.

(57) ABSTRACT

The juice from a spider plant is useful in treating skin and nails. A useful composition preferably includes an admixture of the extract from the spider plant in combination with ALOE VERA. It is emphasized that this abstract is provided to comply with the rules requiring an abstract that will allow a searcher or other reader to quickly ascertain the subject matter of the technical disclosure. It is submitted with the understanding that it will not be used to interpret or limit the scope of meaning of the claims.

8 Claims, No Drawings

TOPICAL TREATMENT FOR SKIN AND NAILS

The present invention is directed to treating skin and nail problems and/or improving the condition of skin and nails.

Skin and nail problems have plagued mankind from time immemorial. In addition there is a desire to improve the appearance of skin and nails.

It has been unexpectedly discovered that a therapeutic composition comprising a therapeutically useful extract of the spider plant can be used to improve the condition of skin and nails.

The therapeutic composition's primary component is an extract in the form of a juice extracted from the roots of the spider plant.

In a preferred embodiment, the juice or extract from the roots of the spider plant can be combined with ALOE VERA to form a liquid lotion, which can be applied as a topical treatment for a wide variety of skin ailments such as eczema, psoriasis and similar dermal conditions, and to obtain relief from itching, burns, insect bites, rashes, dry skin, shingles and similar skin conditions. This same composition was also found to be effective for nail ailments.

The method involves treating a skin or nail ailment through the external administration to skin or nail of a human or animal body in need of such treatment of an effective amount of a therapeutically useful form of an extract of a spider plant. Preferably an extract of the ALOE VERA plant is present in an admixture with the extract of a spider plant. ALOE VERA is readily available in the form of compositions such as lotions in the form of a gel or cream; however, a pure extract of the ALOE VERA plant may be used. Most available commercial ALOE VERA products also contain preservatives so that when such ALOE VERA is used in the admixture with the extract of the spider plant root, the preservative in the ALOE VERA which is now mixed with the extract of the spider plant root provides for longer shelf life of the product. Of course, such preservatives are readily available to mass commercial producers who can then use natural ALOE VERA without the preservative and the preservative can be added as part of the admixture of spider plant extract, ALOE VERA and preservative.

The following example is presented to illustrate one method of making the therapeutic composition in the form of a lotion, which is not intended to be in any way limited thereto, since numerous modifications and variations therein will be apparent to one skilled in the art.

Six to eight two inch roots, called tubers, of one or more adult spider plants are removed from the plant. The common spider plant is also called a "Chlorophytum Comosum" although there are many other varieties of spider plants that could be used. The tubers are washed and the ends of the roots are trimmed. Although it is not necessary, the outer skin of the tubers may also be peeled in the same manner that one might peel a carrot or potato skin. If peeled, the tubers should be washed again. The roots are scrubbed with a clean small brush in fresh water with a drop of liquid soap and a drop of bleach to disinfect. This is typical for the food preparation industry for sanitation purposes. The roots are then rinsed thoroughly. A typical batch with this many roots will generally produce about one cup of roots. These roots are then mixed with an equal volumetric amount of ALOE VERA, which is available as a pure extract but preferably from a composition such as a gel or cream. ALOE VERA is typically made from certified organic ALOE VERA leaves, citric acid, and if a preservative is already added, generally less than one-tenth of 1% pure food grade sodium benzoate and potassium sorbate will be present in the ALOE VERA. As mentioned above, a mass producer will just add the preservative in the admixture.

The roots may be chopped first, mixed with the ALOE VERA and then placed in a processor to finely mix and grind the mixture. Otherwise, the roots may be just added to the ALOE VERA and the mixture can then be placed in a food processor and processed. In this particular batch, processing for about two minutes was deemed to provide a useful liquid composition. The ingredients are then poured into a mesh strainer and the liquid is drained into a bowl placed beneath the strainer. The liquid may be strained again as necessary. In the above example, the liquid was strained-two additional times and poured into a two ounce bottle.

Because the extract itself is the primary beneficial component of the invention, ALOE VERA need not be added and a pure composition of extract may instead be prepared in order to obtain a more concentrated topical treatment.

The extract of the spider plant root should also be available in the leaves of the spider plant; however, the concentration of the amount of extract available from the leaves are considered to be significantly less than that available from the roots themselves.

The strained liquid is to be used only for external treatment. More particularly as an external dermal topical treatment of skin and nails.

When using a processor as mentioned above, it should be noted that while straining the processed product will typically produce a product ideal for liquid, gel or cream form, the product that remains in the strainer may be sufficiently ground to produce a cream form of the topical treatment.

The above composition can be safely used to provide beneficial results on the body. The composition improves the healing growth of skin cells, while removing dry skin cells. No side effects or risks are known. As mentioned above, the composition can be used for the relief of itching, psoriasis and shingles. It is anticipated that the composition, particularly the extract juice itself from the spider plant root, may also be beneficial as a component in an organic skin conditioner, nail therapy treatment, organic nail polish, and nail polish remover.

The above product was used to treat an individual suffering from eczema. Within a few days, a noticeable improvement with no reddening of the skin area occurred. ALOE VERA by itself was used with no noticeable improvement. However, when the composition with the extract of the spider plant was used, improvement of the skin condition was effective.

Other components can be present in the compositions of the present invention such as extracts of roots of other spider plants and extracts of the leaves of spider plants in lieu of or in addition to the above recited components.

It should be understood that the preceding is merely a detailed description of the embodiments to the present invention and that numerous changes to the disclosed embodiments can be made in accordance with the disclosure herein without departing from the spirit and scope of the invention. The preceding description therefore, is not meant to limit the scope of the invention. Rather, the scope of the invention is to be determined only by the appended claims and their equivalents.

What is claimed is:

1. A therapeutic composition for the topical treatment of dermal skin and nail conditions comprising a mixture of a therapeutically useful extract of the spider plant in combination with extract from the ALOE VERA plant.

2. A therapeutic composition for the topical treatment of dermal skin and nail conditions comprising a mixture of a therapeutically useful extract of the spider plant in combination with an ALOE VERA composition.

3. A method of treating a skin or nail ailment by the administration to the skin or nail of a human or animal body in need of such treatment, the method comprising topically applying an effective amount of a therapeutically useful form of an extract of a spider plant.

4. The method according to claim 3, wherein an extract of an ALOE VERA plant is present in an admixture with the extract of a spider plant.

5. The method according to claim 3, wherein an ALOE VERA composition is present in an admixture with the extract of the spider plant.

6. The method according to claim 3, wherein the extract of the spider plant comprises a juice from roots of the spider plant.

7. The method according to claim 3, wherein the extract comprises a juice extracted from the leaves of the spider plant.

8. The method according to claim 3, wherein the extract comprises a juice extracted from combination of roots and leaves of the spider plant.

* * * * *